(12) United States Patent
Borries et al.

(10) Patent No.: US 10,357,378 B2
(45) Date of Patent: Jul. 23, 2019

(54) DEVICES AND METHODS FOR TROCHANTERIC OSTEOTOMY

(71) Applicant: Zimmer, Inc., Warsaw, IN (US)

(72) Inventors: Paul Borries, Columbia City, IN (US); Matthew E. Monaghan, Fort Wayne, IN (US); John Madigan, Derry, NH (US); Robert D. Krebs, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 826 days.

(21) Appl. No.: 14/803,667

(22) Filed: Jul. 20, 2015

(65) Prior Publication Data

US 2016/0022286 A1  Jan. 28, 2016

Related U.S. Application Data

(60) Provisional application No. 62/027,502, filed on Jul. 22, 2014.

(51) Int. Cl.
*A61B 34/10* (2016.01)
*A61F 2/46* (2006.01)
*A61B 17/15* (2006.01)

(52) U.S. Cl.
CPC ............ *A61F 2/4607* (2013.01); *A61B 17/15* (2013.01); *A61B 34/10* (2016.02); *A61B 2034/101* (2016.02)

(58) Field of Classification Search
CPC ... A61B 34/10; A61B 34/25; A61B 2034/101; A61B 2034/105; A61B 2034/107; A61B 2034/252; A61B 2034/2048; A61B 2034/2059; A61B 2034/2072; A61B 17/155; A61F 2/4657
See application file for complete search history.

(56) References Cited

U.S. PATENT DOCUMENTS

| 5,007,936 | A  | * | 4/1991  | Woolson | A61B 17/1746 |
|           |    |   |         |         | 128/898 |
| 6,236,875 | B1 | * | 5/2001  | Bucholz | A61B 5/0064 |
|           |    |   |         |         | 600/407 |
| 6,740,120 | B1 | * | 5/2004  | Grimes  | A61B 17/15 |
|           |    |   |         |         | 623/22.12 |
| 6,827,723 | B2 | * | 12/2004 | Carson  | A61B 34/20 |
|           |    |   |         |         | 606/130 |
| 7,318,827 | B2 | * | 1/2008  | Leitner | A61B 17/15 |
|           |    |   |         |         | 600/427 |
| 2005/0267484 | A1 |  | 12/2005 | Menzner |  |

OTHER PUBLICATIONS

Stepped Osteotomy of the Trochanter for Stable, Anatomic Refixation, Clinical Orthopaedics and Related Research, Mar. 2009; 467(3); 732-738; Bastian et al.*

* cited by examiner

*Primary Examiner* — Anu Ramana
(74) *Attorney, Agent, or Firm* — Schwegman Lundberg & Woessner, P.A.

(57) ABSTRACT

Templating software can determine and visually depict the location and size of cuts in a trochanteric osteotomy, including an extended trochanteric osteotomy. The software can also calculate the size and area of fixation for a newly implanted prosthesis, based upon which the new prosthesis that will be implanted in a particular patient can be selected. Additionally, an adjustable cut guide can stabilize and guide the cuts during the procedure.

11 Claims, 10 Drawing Sheets

DEVICES AND METHODS FOR TROCHANTERIC OSTEOTOMY

PRIORITY APPLICATIONS

This application claims the of priority benefit under 35 U.S.C. 119(e) to U.S. Provisional Application No. 62/027,502, filed on 22 Jul. 2014; which application is incorporated herein by reference in its entirety.

BACKGROUND

Femoral revision hip arthroplasty is a procedure to repair or replace a compromised or failed hip stem of a proximal femoral replacement prosthesis. In some cases, the procedure includes removing a failed prosthesis. One method for removing the existing prosthesis is an extended trochanteric osteotomy (ETO). An ETO is a cut in the femur from the greater trochanter down to the tip of the stem of the existing femoral prosthesis to remove a window of bone for easier access to the existing implant.

DESCRIPTION

Total hip replacement surgery is commonly performed to alleviate pain and loss of function in injured and diseased hip joints. During this surgery, the articulating surfaces of the hip joint are replaced with prosthetic bearing components. The replacement components can include a femoral component having a convex bearing surface and an acetabular cup component having a mating concave bearing surface. The femoral bearing is configured to rotate in the acetabular bearing in a manner that approximates the rotation of a patient's femoral head in the acetabulum of the hip.

Over time the prosthetic components can deteriorate in structure and/or function and may need to be repaired or replaced. In some such circumstances, a patient may undergo a femoral revision hip arthroplasty to repair or replace, for example, a compromised or failed stem of a proximal femoral replacement prosthesis. In some cases, the procedure includes removing a failed prosthesis. One method for removing the existing prosthesis is an ETO.

Examples according to this disclosure are directed to devices and methods for use in a trochanteric osteotomy, including an ETO. For example, templating software can determine and visually depict the location and size of the osteotomy cuts. The software can also calculate the size and area of fixation for a newly implanted prosthesis stem, based upon which the new prosthesis that will be implanted in a particular patient can be selected. Additionally, an adjustable cut guide can stabilize and guide the cuts during the procedure.

Figure 1A:
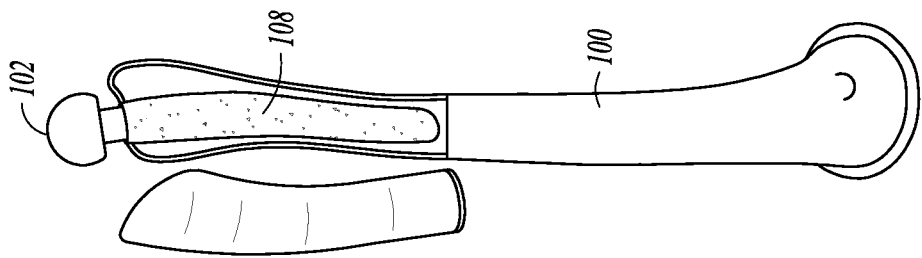
FIGS. 1A-1D depict an ETO from anterior, posterior, medial, and lateral perspectives of a femur including a proximal femoral prosthesis.
Figure 1B:
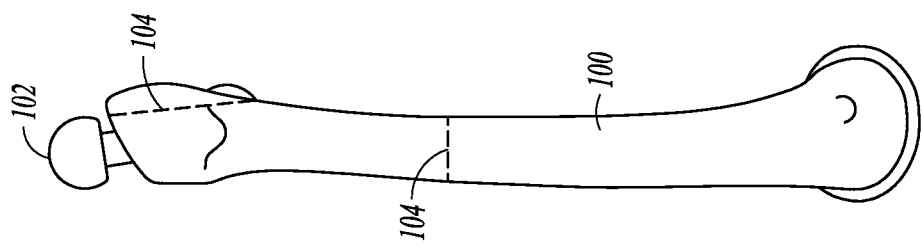
Figure 1C:
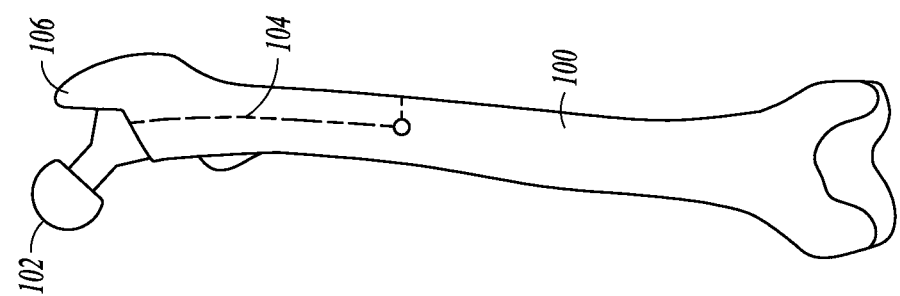
Figure 1D:
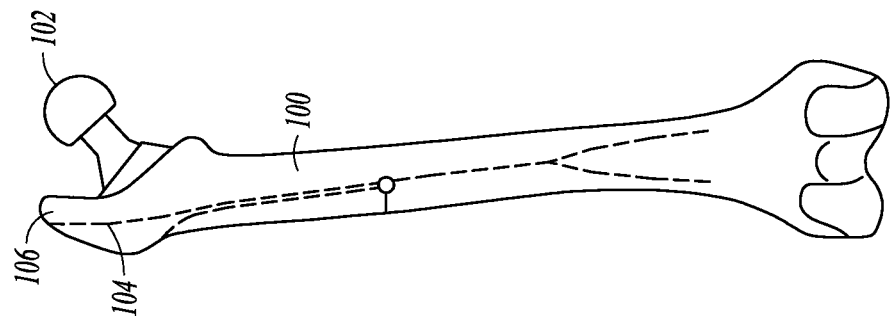
Figure 2A:
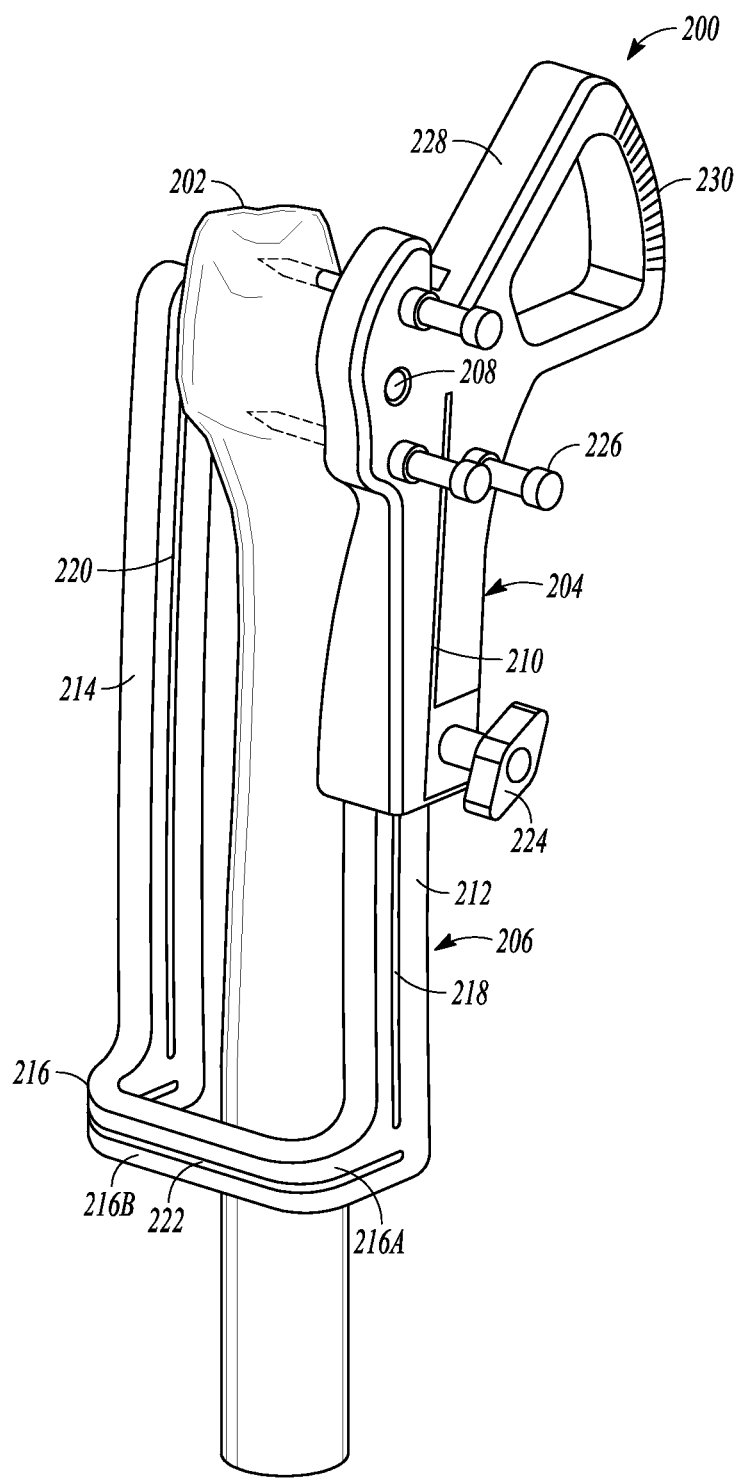
FIGS. 2A-2D depict an example adjustable osteotomy cut guide device affixed to the proximal end of a femur.
Figure 2B:
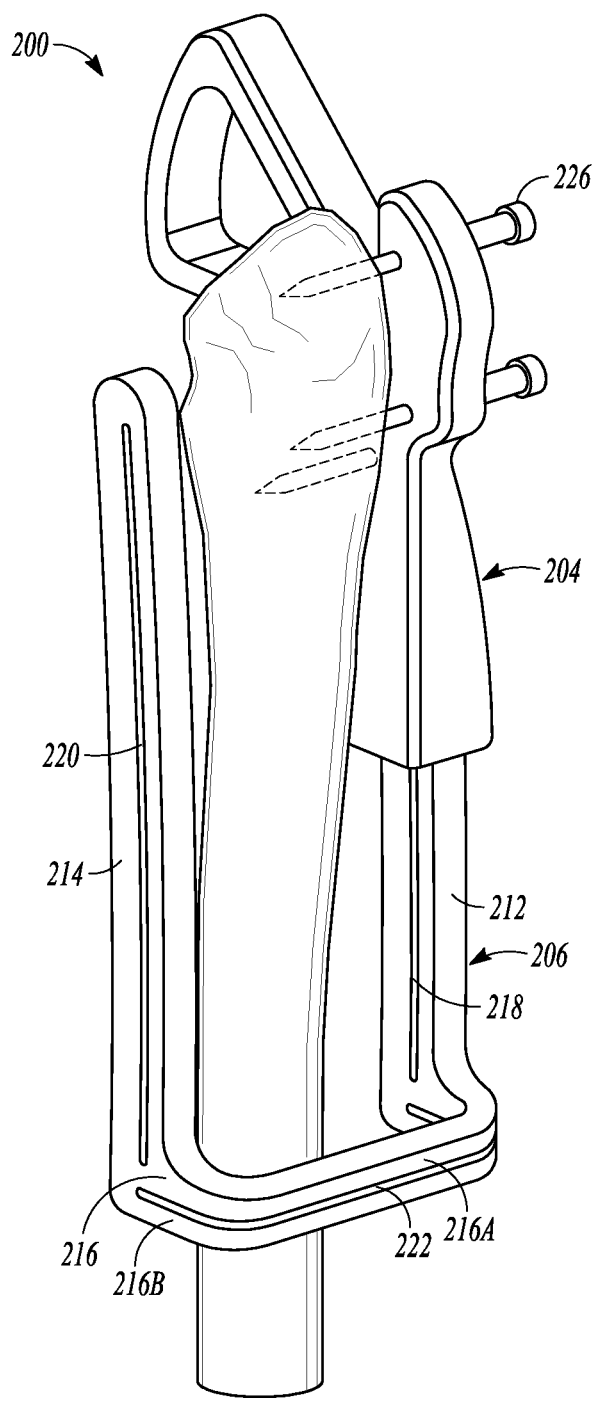
Figure 2C:
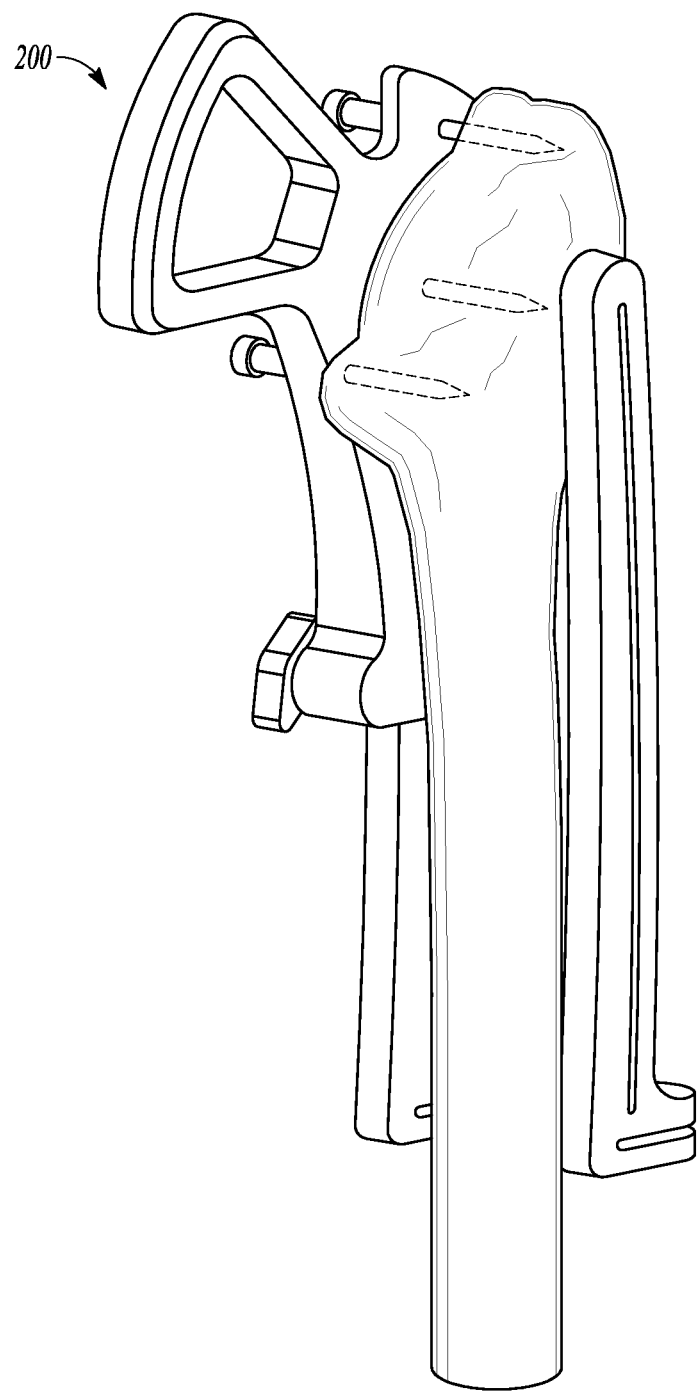
Figure 2D:
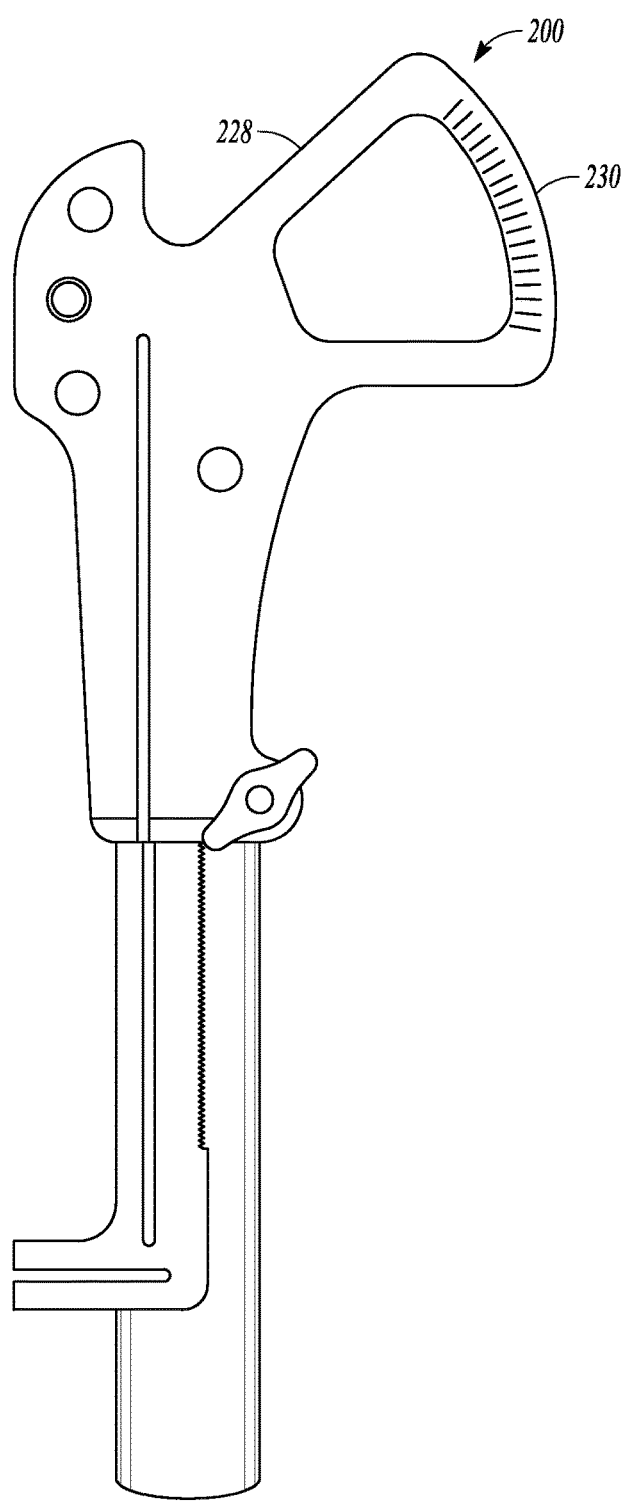

FIGS. 1A-1D depict an ETO from anterior, posterior, medial, and lateral perspectives of a femur 100 including a proximal femoral prosthesis 102. In FIGS. 1A-1D, a portion of the patient's femur 100 is cut and removed to repair and/or replace the compromised femoral prosthesis 102. FIGS. 1A-1C depict cut line 104, along which a surgeon may make the ETO cut of femur 100. FIG. 1D depicts the osteotomy of femur 100 when cut along cut line 104 from the greater trochanter 106 to the tip of stem 108 of femoral prosthesis 102.

During the ETO procedure, the surgeon can employ an oscillating saw or other instrument to make two longitudinal cuts from greater trochanter 106 down to the tip of stem 108 on both the anterior and posterior sides of femur 100. The surgeon can then make one lateral cut from the outer surface of femur 100 near the tip of stem 108 radially inward to the ends of the two longitudinal cuts. After performing the ETO cut in this or another similar manner, the surgeon can remove the cut portion of the femur to inspect, repair, and/or remove femoral prosthesis 102.

The orthopedic surgeon performing the ETO is presented with a number of challenges, including determining the location and length of the ETO cut, as well as marking and executing the cut on the patient's femur. Examples according to this disclosure can be employed to assist the surgeon during the ETO.

In one example, an adjustable cut guide is configured to be attached to the proximal end of the femur. The cut guide includes a number of guides for the longitudinal and lateral ETO cuts. The length of the longitudinal guides, for example, anterior and posterior guides can be adjustable to adapt one cut guide to multiple patient anatomies. The cut guide is affixed to a portion of the femur and then adjusted to the proper length prior to the surgeon executing the ETO cuts.

Additionally, software, which is sometimes referred to herein as "templating software," can be configured to determine the location of the ETO cuts, calculate the proper length of the longitudinal cuts, and calculate the size of the replacement hip prosthesis stem to improve fixation after the revision is complete. The templating software can be configured to output parameters for proper osteotomy cuts based on radiographic images of the prosthesis to be removed. The surgeon can begin the ETO by obtaining a radiographic image of the femur with the existing femoral prosthesis that will be removed. The radiographic image can be input into the templating software, which the surgeon can employ to mark landmarks of the femur such as the greater trochanter, lesser trochanter, and distal tip of the existing femoral prosthesis stem. The software can then determine and visually depict osteotomy cut lines on the radiographic image depicting particular patient anatomy. The surgeon can also employ the software to manipulate the cut lines automatically determined by the software. Once the proposed cut lines are finalized using the templating software, the software can output parameters by which the surgeon can execute the ETO cuts, including the length of the anterior and posterior longitudinal cuts.

The templating software can also be employed to plan the new revision femoral prosthesis. Using the radiographic image and landmark points on the femur, the software can generate and visually depict a fixation zone that will extend a target length beyond the tip of the existing prosthesis stem, for example, 4-6 cm in length. The fixation zone generated by the software can also cover the width of the femoral canal. The surgeon can then manipulate the fixation zone using the templating software to the appropriate location in the femur to increase the chances that the ETO and all femoral defects are bypassed by the planned revision prosthesis stem. Based on the fixation zone generated by the software and adjusted by the surgeon, the software can output a matching diameter and length for the new prosthesis stem.

FIGS. 2A-2D depict an example adjustable osteotomy cut guide device 200 affixed to the proximal end of a femur 202. Cut guide 200 includes first member 204 and second member 206. First member 204 includes a number of fixation apertures 208 and a longitudinal cut guide 210. Longitudinal cut guide 210 is in the form of a longitudinal slot, which may be straight or curved. However, in other examples, a longitudinal cut guide could be in the form of an open face against which a surgeon could place one side of a saw or other instrument used to execute a bone cut.

Second member 206 includes first and second elongated legs 212 and 214, both of which are connected at the distal ends to a "U" shaped member 216. U-shaped member 216 extends approximately perpendicularly from the distal ends of legs 212 and 214. First and second legs 212 and 214 include longitudinal cut guides 218 and 220, respectively. Longitudinal cut guides 218 and 220 can be employed by the surgeon to execute the anterior and posterior longitudinal cuts of an ETO, for example. Longitudinal guides 218 and 220 are in the form of longitudinal slots, which may be straight or curved. However, in other examples, one or both of guides 218 and 220 could be in the form of an open face against which a surgeon could place one side of a saw or other instrument used to execute a bone cut. U-shaped member 216 includes a lateral cut guide 222, which is in the form of a slot that divides U-shaped member 216 into two generally U-shaped portions 216a and 216b.

First elongated leg 214 of second member 206 is connected to first member 204. Second member 206 is connected to first member 204 such that longitudinal cut guide 210 of first member is substantially aligned with longitudinal cut guide 218 of first leg 214 of second member 206. In this manner, longitudinal cut guide 210 of first member 204 and longitudinal cut guide 218 of second member 206 together form one longitudinal cut guide, which can extend, for example, from the lesser trochanter to the tip of the existing femoral prosthesis stem on the anterior side of femur 202.

Second member 206 is movably connected to first member 204 to allow osteotomy cut guide device 200 to be adjusted to different patient anatomies. Second member 206 can be configured to slide longitudinally, for example, proximally and distally with respect to first member 204. Second member 206 can therefore be moved with respect to first member to change the length of the posterior and anterior longitudinal cuts of an ETO. In the example of FIGS. 2A-2D, the proximal end of leg 212 of second member 206 is received and can slide within a pocket formed in a portion of first member 204. In other examples, however, the structural connection between first and second members 204 and 206 can differ. For example, longitudinal leg 212 of second member can be received in a slot in first member 204, including forming a tongue and groove connection therebetween.

Osteotomy cut guide device 200 can also include a lock mechanism, which can be engaged and disengaged to adjust the position of second member 206 relative to first member 204. Example device 200 includes wing nut 224, which can be loosened by the surgeon to slide second member 206 relative to first member 204 to adjust the length of longitudinal cuts. Wing nut 224 can then be tightened to fix the position of second member 206 with respect to first member 204 at a desired longitudinal cut length. Other locking mechanisms could also be employed.

For example, example osteotomy cut guide devices can include a ratchet lock mechanism. One of first and second members 204 and 206 can include ratchet teeth and the other of first and second members 204 and 206 can include a releasable spring loaded pawl. In an example, the second member 206 can be moved in one direction, e.g., proximally into a plurality of discrete positions as successive ratchet teeth successively engage the spring loaded pawl. In this example, second member 206 can only move freely in one direction as each successive ratchet tooth engagement substantially prevents movement in the opposite direction. The pawl can be connected to a trigger to disengage the pawl from the ratchet teeth and allow second member 206 to move relative to first member 204 in the opposite, for example, distal direction.

In another example, a spring loaded pin can be engaged, for example, pulled by the surgeon to allow second member 206 to move relative to first member 204. The pin can be disengaged by the surgeon and then be biased to be received within one of a plurality of holes to lock second member 206 at a plurality of discrete positions relative to first member 204.

In use, cut guide device 200 is located and attached to femur 202. For example, fixation apertures 208 or other landmarks on device 200 can be aligned to anatomical landmarks, including, for example, the greater and lesser trochanter. Once device 200 is located properly relative to femur 202, device 200 can be affixed to femur by pins 226, screws, or other mechanisms, for example, through fixation apertures 208. After cut guide device 200 is located and attached to femur 202, second member 206 can be moved relative to first member 204 to set the length of the longitudinal cuts of the osteotomy. The surgeon can then employ the combination of longitudinal cut guide 210 of first member 204 and longitudinal cut guide 218 of second member to execute one longitudinal cut, employ longitudinal cut guide 220 to execute another longitudinal cut, and employ lateral cut guide 222 to execute the lateral cut to complete the ETO cuts.

The length of second leg 214 of second member 206 can be set such that leg 214 and associated cut guide 220 extends to or near the proximal end of femur 202 when second member 206 is fully distally extended relative to first member 204. In this manner, cut guide 220 can extend the full length of the required osteotomy cut in all of the different adjustable positions of second member 206 relative to first member 204.

Cut guide device 200 and other cut guide devices in accordance with this disclosure can be fabricated from a variety of materials and by a variety of manufacturing techniques. Cut guides in accordance with this disclosure can be fabricated from a number of different biocompatible materials, including short term contact biocompatible metals, plastics, or composites. For example, cut guides in accordance with this disclosure can be fabricated from stainless steel, polyphenylsulfone, or other like materials. Example cut guides can be machined, cast, or fabricated using other techniques appropriate for manufacturing such devices.

Example cut guide device 200 includes location guide 228 to assist in proper location and attachment of the cut guide to femur 202. Location guide 228 includes an arcuate portion 230. In some examples, arcuate portion 230 of location guide 228 can include marks like radial lines that can be employed to help position cut guide device 200 using the center line of the neck of the existing femoral prosthesis to be removed. Marks on arcuate portion 230 can also to help identify the implant by determining the neck angle. In some examples, arcuate portion 230 includes relatively longer radial lines at common angles for implants and smaller radial lines to help better determine other conditions encountered during a particular ETO, including, for example, custom implants, changes from implantation, etc.

Examples according to this disclosure also include devices, systems, and methods that can be used to implement templating software for use in connection with trochanter osteotomies, including ETOs. FIGS. 3-7 depict a portion of the graphical user interface (GUI) of example templating software according to this disclosure. The templating software depicted in and described with reference to FIGS. 3-7 can be employed in conjunction with a osteotomy cut guide device in accordance with this disclosure, including, for example, cut guide device 200.

Figure 3:
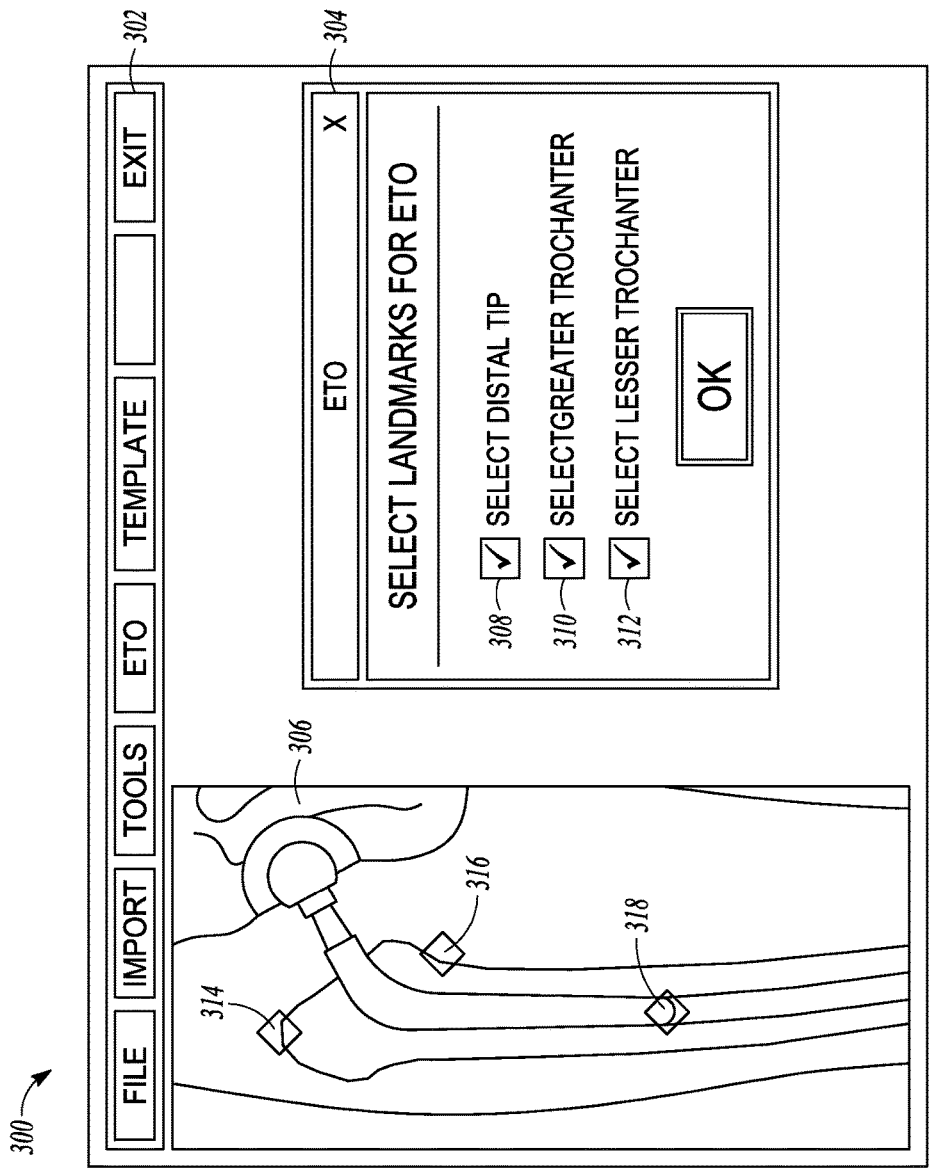
FIGS. 3-7 depict graphical user interfaces of an example templating software system that can be configured to determine and visually depict the location and size of osteotomy cuts, and calculate the size and area of fixation for a newly implanted femoral prosthesis.

FIG. 3 depicts GUI 300 of example templating software in accordance with this disclosure. GUI 300 includes menu 302, control window 304, and interactive digital anatomical image 306. The templating software including GUI 300 can be employed in conjunction with anatomical visualization devices and methods. In one example, the software is employed in conjunction with a radiograph device that captures and outputs an image representing actual patient anatomy via, for example, a cathode ray tube (CRT), liquid crystal display (LCD), or light emitting diode (LED) monitor. The templating software can receive a digital radiographic image from the radiograph device and visually depict the image via GUI 300.

In the example of FIG. 3, interactive radiograph image 306 visually depicts the proximal portion of a patient's femur with a femoral prosthesis that can be the target of a revision hip arthroplasty. Radiograph image 306 can be interactive, including, allowing placement and manipulation of visual elements, including, anatomical landmarks. Menu 302 and control window 304 are also interactive elements of GUI 300. Menu 302 can include a number of selectable menu items, for example, "File," "Import," "Tools," "ETO," "Template," and "Exit," one or more of which may be selected to execute a function including causing the software to visually depict sub-menu items like "File→Save." In other examples, menu 302 of GUI 300 could include additional and/or different menu items than those shown in the example of FIG. 3. Control window 304 includes input controls like check boxes (and/or buttons, drop-down lists, radio buttons, etc.), which can be selected to instruct the templating software to execute particular functions.

In FIG. 3, GUI 300 is employed to begin planning the cuts of an ETO. Upon initiating the procedure in the templating software, GUI 300 generates control window 304, which visually depicts inputs corresponding to landmark selections. Check-box control 308 corresponds to a selection on radiograph image 306 corresponding to the distal tip of the existing femoral prosthesis stem. Check-box controls 310 and 312 correspond to selections on radiograph image 306 corresponding to the greater and lesser trochanter, respectively.

An input device such as a mouse, stylus, or a touchscreen can be employed to provide indications of the requested landmarks in radiographic image 306, which indications are received by the templating software via the input device. The templating software then generates visual depictions of each landmark overlaid on radiographic image 306. In the example of FIG. 3, GUI 300 has generated, based on indications of input selections, three visual landmark indications 314, 316, and 318 corresponding to the greater trochanter, lesser trochanter, and tip of the prosthesis stem, respectively.

Once the three landmark selections have been made, the "OK" button 320 in control box 304 can be selected with an input device. The software receives an indication of the selection and then executes one or more functions. In one example, the templating software calculates the length of the longitudinal cuts of the ETO and generates the GUI depicted in FIG. 4.

Figure 4:
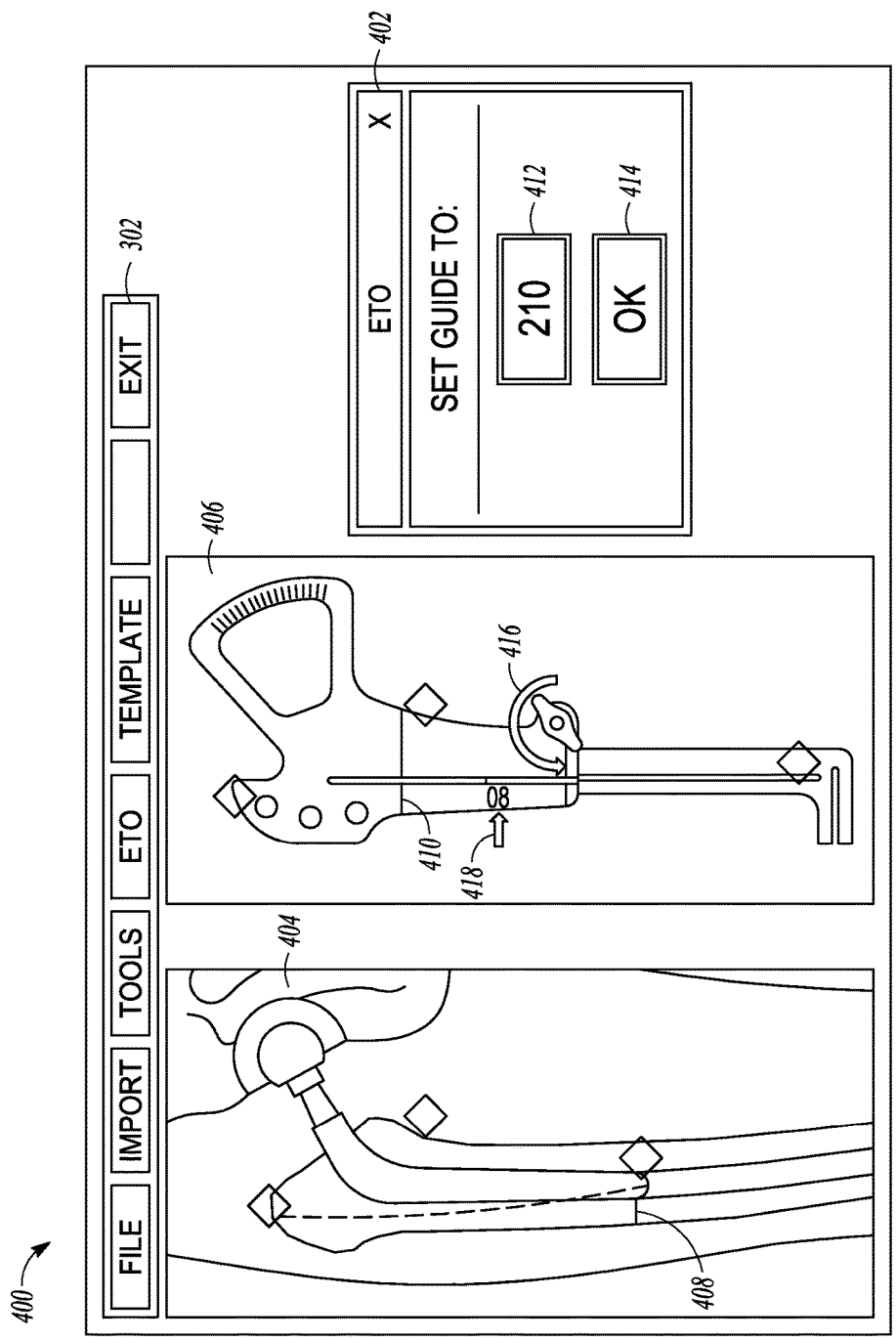

FIG. 4 depicts GUI 400 of example templating software in accordance with this disclosure. GUI 400 is similar to GUI 300 and includes menu 302, control window 402, and interactive digital images 404 and 406. In the example of FIG. 4, interactive image 404 can be a radiograph image that visually depicts the proximal portion of the patient's femur with the femoral prosthesis in a similar manner as image 306 of FIG. 3. Radiograph image 404 can be interactive, including, allowing placement and manipulation of visual elements, including, anatomical landmarks.

Templating software in accordance with this disclosure can be configured to determine and visually depict the cut line of an ETO cut or other type of orthopedic cut employed in different procedures. In the example of FIG. 4, the templating software has determined and visually represents cut line 408 overlaid on radiograph image 404. The templating software can employ a number of different types of algorithms to determine and visually depict ETO cuts via GUI 400 or another GUI of the software. In general, however, templating software in accordance with this disclosure can be configured to determine the cut line based on the indications of anatomical landmarks 314, 316, and 318 corresponding to the greater trochanter, lesser trochanter, and tip of the prosthesis stem, respectively, received by the input device. For example, in FIG. 4, the longitudinal ETO cut portion of cut line 408 extends from greater trochanter landmark 314 along a curved trajectory to the tip of the stem landmark 318. The templating software can also employ image analysis algorithms to determine the cut line, including, e.g., analyzing pixel data associated with radiographic images of patient anatomy to discriminate different types of patient tissue from one another and from implanted prostheses based the relative radiolucency of such structures included in the images analyzed by the software.

In the example of FIG. 4, image 406 of GUI 400 optionally visually depicts an adjustable ETO cut guide device in accordance with this disclosure (similar to example cut guide 200 of FIGS. 2A-2D) to assist the surgeon in placement and adjustment of the cut guide. GUI 400 overlays the anatomical landmarks 314, 316, and 318 on the cut guide to visually indicate placement of the cut guide on the patient anatomy. In the example cut guide shown in image 406, the location of the lesser trochanter and associated landmark 316 corresponds with a lateral ridge 410 in the cut guide. However, in other examples, the location of the lesser trochanter (or other anatomical landmarks) relative to an adjustable ETO cut guide could be achieved with other structures on the guide, including, e.g., holes for screws or pins used to attach the cut guide to the patient's femur like one of fixation apertures 208 of example guide 200 of FIGS. 2A-2D.

GUI 400 can be employed to continue planning the cuts of the ETO. Having determined the trajectory, location, and length of the ETO cut, GUI 400 of the templating software generates control window 402, which visually depicts an input corresponding to a cut length setting on an adjustable cut guide employed in conjunction with the templating software. In the example of FIG. 4, control window 402 provides text box 412 and "OK" control button 414 to inform the surgeon or other clinician to what length to set the adjustable ETO cut guide.

In some examples, templating software and the associated cut guide can be configured to adjust to different absolute values of length, e.g., values of length in inches, centimeters, or some other unit of measurement. In other examples including the example of FIG. 4, however, the templating software and associated cut guide transforms the absolute length to an index value. The length index can be formulated in a variety of ways, including, e.g., transforming different length values into different letters, e.g. index values of A, B, C, D, etc. In the example of FIG. 4, the length index is an index of integers like 1, 2, 3, 4, etc. or 10, 20, 30, 40, etc., each of which index value corresponds to an absolute length or range of absolute lengths. The templating software can output the ETO cut length by employing an algorithm that correlates different cut lengths or ranges of lengths with each of a number of index values.

Having received the cut guide length setting from the templating software, the surgeon can adjust an ETO cut guide in accordance with this disclosure to the appropriate index mark on the cut guide to set the length of the actual cut on the femur of the patient. In the example of FIG. 4, GUI 400 visually depicts some arrow images 416 and 418 overlaid on cut guide image 406 to inform the surgeon how to unlock and adjust the guide and where to look for the length index value on the guide, respectively.

After the templating software has determined the trajectory, location, and length of the ETO cut and output the cut guide length setting, the "OK" button 414 in control box 402 can be selected with the input device. The software receives an indication of the selection and then executes one or more functions. In one example, the templating software generates the GUI depicted in FIG. 5 after receiving the indication of selection of "OK" button 414 in control box 402 of GUI 400 in FIG. 4.

Figure 5:
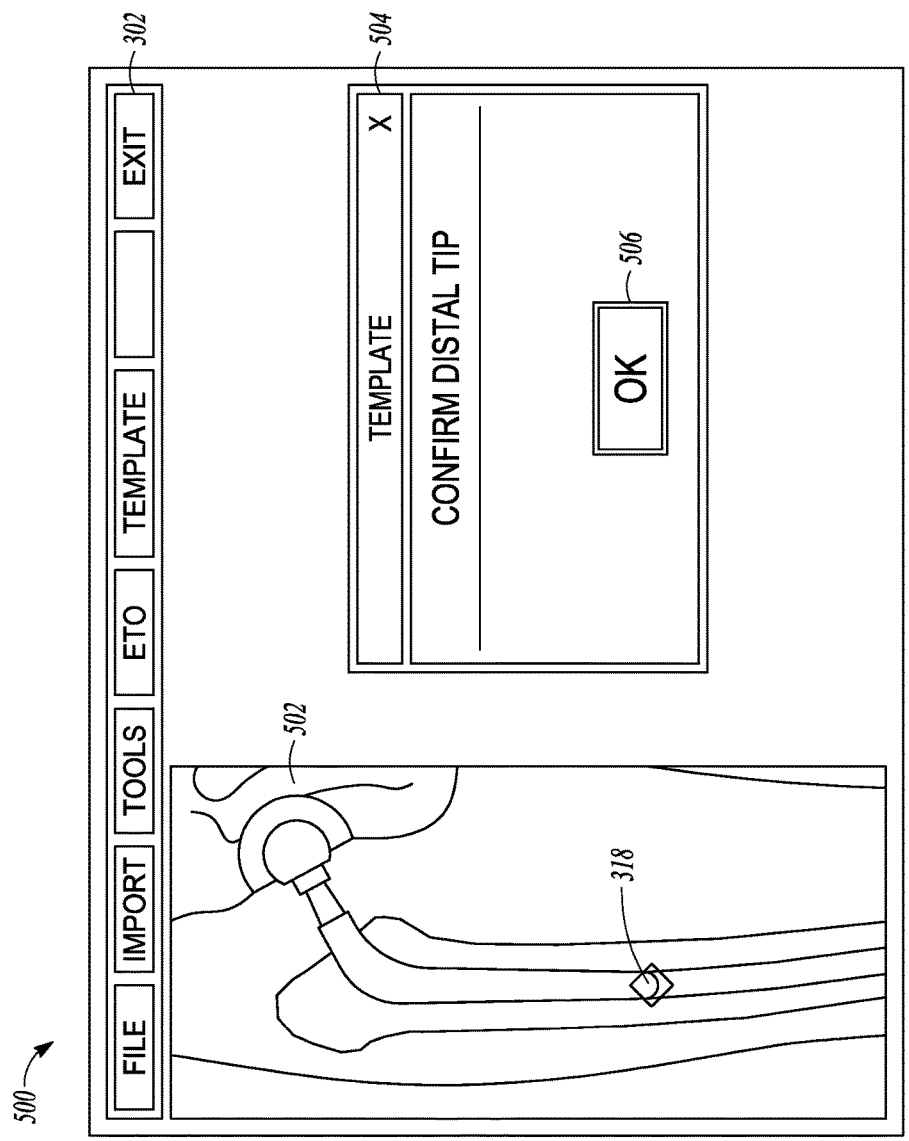

In addition to determining and visually depicting the location and length of osteotomy cuts, examples according to this disclosure include software that is configured to help plan and calculate the size and area of fixation for a newly implanted prosthesis stem, based upon which the software can calculate the size of the new prosthesis that will be implanted in a particular patient. FIG. 5 depicts GUI 500 generated by the example templating software. GUI 500 includes radiographic image 502, menu 302, and control box 504. GUI 500 can automatically generate and visually depict radiographic image 502 of the patient's femur including stem tip landmark 318. GUI 500 can then prompt the surgeon or other user to confirm that the location of landmark 318 is correct or to move the landmark and then confirm the tip of the stem has been properly located. The "OK" button 506 in control box 504 can be selected with the input device. The software receives an indication of the selection and then executes one or more functions. In one example, the templating software generates the GUI depicted in FIG. 6 after receiving the indication of selection of "OK" button 506 in control box 504 of GUI 500 in FIG. 5.

Figure 6:
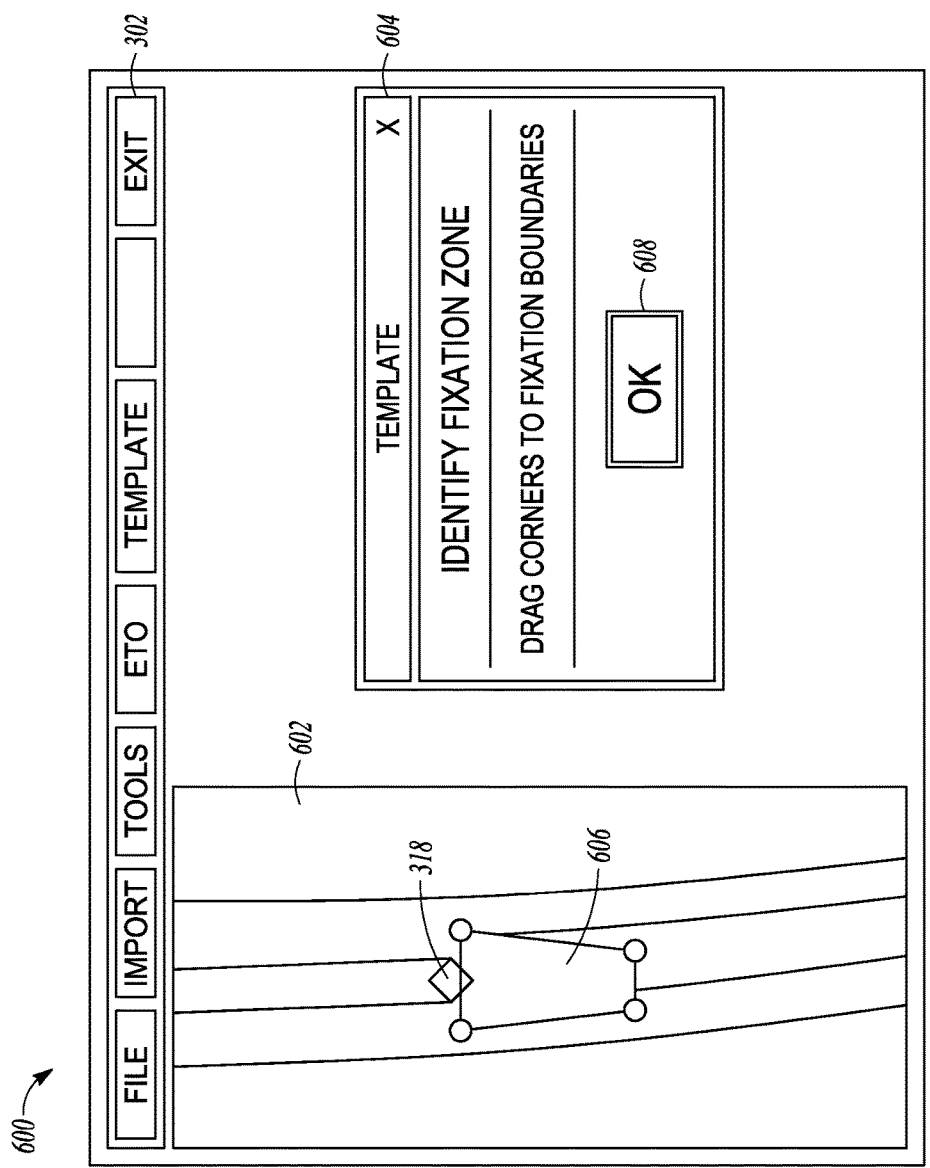

FIG. 6 depicts GUI 600 generated by the templating software to assist the surgeon in planning an area of fixation for a revision hip prosthesis, based upon which the software can calculate the size of the new prosthesis that will be implanted in the patient. GUI 600 includes radiographic image 602, menu 302, and control box 604. Radiographic image 602 can be an interactive radiograph image that visually depicts a portion of the patient's femur adjacent the stem of the existing femoral prosthesis. As illustrated in the example of FIG. 6, templating software has determined and causes GUI 600 to visually depict stem tip landmark 318 and a default fixation zone 606 overlaid on image 602.

To increase the stability and increase the chances of proper fixation of the revision prosthesis, the stem of the prosthesis may need to extend beyond the tip of the existing stem by a certain distance and may need have a width/diameter that is oversized relative to the diameter of the intramedullary canal of the femur of the patient. Templating software in accordance with this disclosure can be configured to analyze digital images of patient anatomy, e.g. image 602, and calculate and visually depict a default fixation zone based on, inter alia, an approximate centerline of the femur, the length of current stem, the location of tip of the existing prosthesis, and the diameter of the intramedullary canal.

In one example, the templating software analyzes image 602 to determine the approximate location of the existing stem based on landmark 318 and the width of the intramedullary canal. The templating software can analyze pixel data associated with image 602 to discriminate between areas including femoral bone tissue, generally hollow areas and/or areas including soft tissue within the femur, and the existing metallic prosthesis stem. The templating software can then generate an adjustable fixation zone that extends longitudinally from the tip of the existing stem by a target length and extends laterally by a target width.

The templating software can generate the default fixation zone in a number of different ways. The recommended length of distal fixation in a revision hip anthroplasty may be, in some cases, from approximately 4 centimeters (cm) and to approximately 6 cm. Additionally, the recommended revision prosthesis stem diameter may be oversized to the intramedullary canal by approximately 1 millimeter (mm). In such cases, the templating software can be configured to size the default fixation zone to a length, e.g., 5 cm, which the surgeon or other use can then adjust as needed via the input device and interactive image 602 of GUI 600. The software can also size the width/diameter of the fixation zone to a value of 1 mm plus the diameter of the intramedullary canal, which the surgeon or other user can then adjust as needed via the input device and interactive image 602 of GUI 600. In another example, the software sizes the width/diameter of the fixation zone to a fixed value, e.g., based on statistical data of patient anatomies, which the surgeon or other user can adjust as needed via the input device and interactive image 602 of GUI 600. In the example of FIG. 6, fixation zone 606 can be adjusted by using the input device to drag the corners of the fixation zone.

The "OK" button 608 in control box 604 can be selected with the input device after the appropriate fixation zone 606 size has been input. The software receives an indication of the fixation zone 606 adjustments and the "OK" button 608 selection and then executes one or more functions. In one example, the templating software generates the GUI depicted in FIG. 7 after receiving the indication of selection of "OK" button 608 in control box 604 of GUI 600 in FIG. 6.

Figure 7:
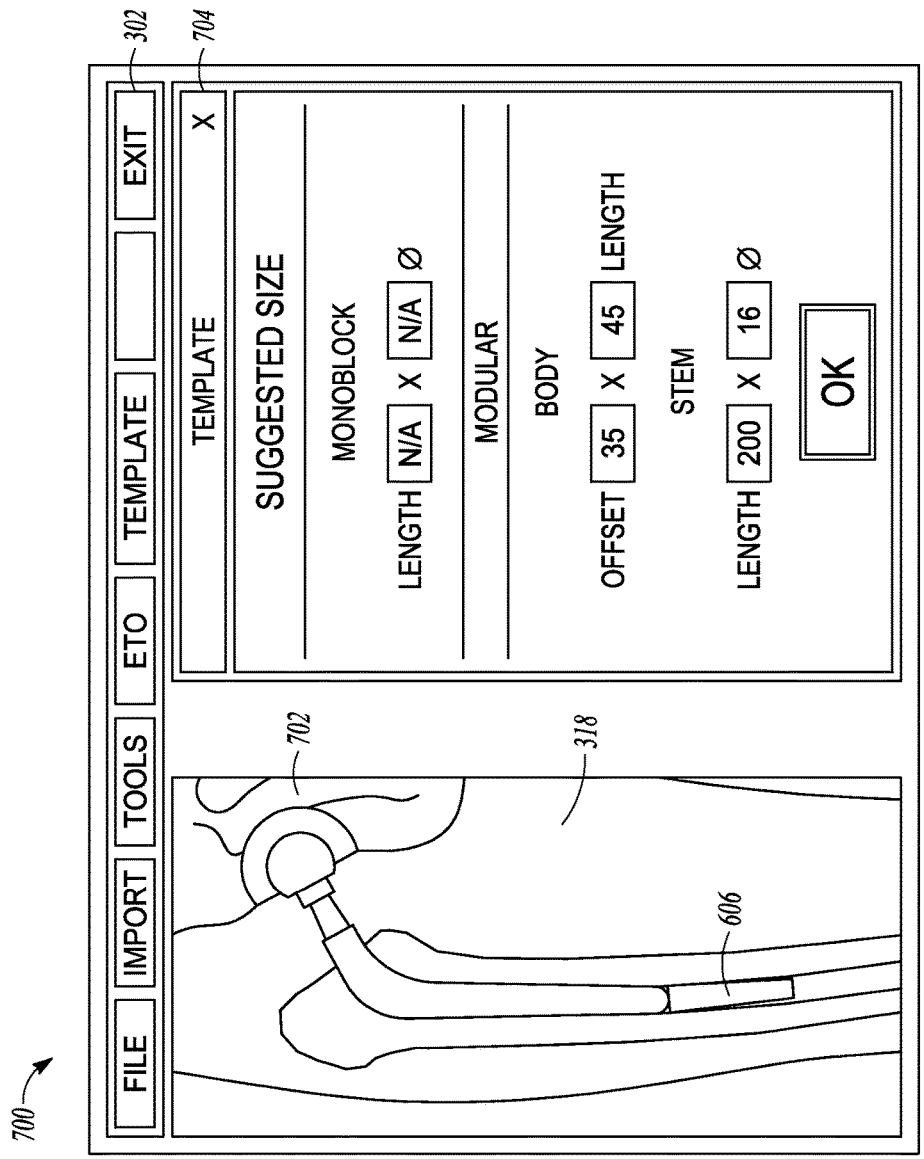

FIG. 7 depicts GUI 700 generated by the templating software to provide one or more parameters associated with the recommended size of the new prosthesis that will be implanted in the patient. GUI 700 includes radiographic image 702, menu 302, and control box 704. Radiographic image 702 can be an interactive radiograph image that visually depicts the existing femoral prosthesis, the proximal portion of the femur, and fixation zone 606.

The templating software is configured to receive the default or adjusted fixation zone 606 from GUI 600 and automatically calculate the size of the revision prosthesis to be implanted in the patient. In one example, the templating software includes an algorithm that calculates a recommended size for the revision prosthesis based on, inter alia, the fixation zone size, the length of the existing stem, the location of the tip of the existing stem, the length of the proximal portion of the femur, as well as other characteristics of, e.g., patient anatomy and/or the existing femoral prosthesis. In FIG. 7, GUI 700 outputs the parameters associated with the revision prosthesis determined by the software. In the example of FIG. 7, control box 704 outputs the prosthesis body offset and length and the stem length and outside diameter determined by the templating software.

In the example of FIG. 7, the existing femoral prosthesis is a modular implant and thus the templating software also calculates the body offset and length of the modular implant and outputs the calculated values via control box 704 of GUI 700. Some femoral prostheses include a modular stem having a two piece construct including a proximal body and a distal stem. The distal stem is selected to fit the size of the femur for fixation, and the proximal body is selected to achieve the correct center for the head of the existing prosthesis. A monoblock stem is all one piece so you cannot independently select the distal and proximal components.

The proximal body offset and length of the modular implant of the example of FIG. 7 can be determined by the templating software based on the location of fixation zone 606. For example, the software can use the location of fixation zone 606 along with the acetabular center of rotation (i.e. head center) to determine the overall stem length, which is a total of distal stem length and proximal body length in a modular stem. The body offset (distance from the stem center line to the head center) can be calculated in the same manner.

In another example in which the templating software is employed for an ETO including a monoblock implant, the body offset and length are inapplicable. In such an example, templating software can determine the length and diameter of the monoblock implant and output the values via control box 704 of GUI 700.

After receiving the revision prosthesis recommendation from the templating software, the surgeon can proceed with the revision hip anthroplasty. Additionally, the software can be configured to store and retrieve data associated with the procedure, including, e.g., the radiographic images and associated anatomical landmarks and fixation zone, as well as the recommended cut length and associated cut guide setting and the revision prosthesis parameter recommendations.

ADDITIONAL NOTES & EXAMPLES

Example 1 is an adjustable cut guide device configured to be attached to a proximal end of a femur, the cut guide device can include: a first member configured to be attached to the proximal end of the femur; a second member movably attached to the first member, the second member comprising: a longitudinal cut guide; and a lateral cut guide, wherein the second member is configured to move relative to the first member to adjust a length of the longitudinal cut guide.

In Example 2, the device of Example 1, wherein the first member comprises one or more fixation apertures configured to receive one or more fasteners to attach the first member to the proximal end of the femur.

In Example 3, the device of Example 1 or Example 2, wherein the longitudinal cut guide comprises a first longitudinal cut guide and the first member comprises a second longitudinal cut guide aligned with the first longitudinal cut guide.

In Example 4, the device of any of Examples 1-3, wherein the longitudinal cut guide comprises at least one of a slot in which a surgical cutting instrument can be received or a surface against which a surgical cutting instrument can be placed.

In Example 5, the device of any of Examples 1-4, wherein the second member comprises first and second longitudinal legs, at least one of the first and second longitudinal legs comprising the longitudinal cut guide; and a U-shaped member connected between distal ends of the first and second longitudinal legs, the U-shaped member comprising the lateral cut guide.

In Example 6, the device of Example 5, wherein the longitudinal cut guide comprises a first longitudinal cut guide and the second member comprising a second longitudinal cut guide, one of the first and second longitudinal legs comprising the first longitudinal cut guide and the other of the first and second longitudinal legs comprising the second longitudinal cut guide.

In Example 7, the device of Example 5 or Example 6, wherein the lateral cut guide comprises a slot that divides the U-shaped member into two U-shaped portions.

In Example 8, the device of any of Examples 1-7, wherein the second member is received and configured to slide within a pocket in the first member.

In Example 9, the device of any of Examples 1-8, wherein the second member is received and configured to slide within a slot in the first member.

In Example 10, the device of Example 9, wherein a portion of the second member forms a tongue received in a groove formed in the slot in the first member.

In Example 11, the device of any of Examples 1-10, further comprising a lock mechanism that substantially prevents relative movement between the first and second members.

Example 12 is a method that can include: attaching an adjustable cut guide device to a proximal end of a femur to perform an extended trochanteric osteotomy (ETO), the cut guide device comprising: a first member configured to be attached to the proximal end of the femur; and a second member movably attached to the first member, the second member comprising a longitudinal cut guide and a lateral cut guide; and moving the second member relative to the first member to adjust a length of the longitudinal cut guide.

In Example 13, the method of Example 12, further comprising inserting a surgical cutting instrument into the longitudinal cut guide to guide a longitudinal cut in the femur.

In Example 14, the method of Example 12 or Example 13, further comprising inserting a surgical cutting instrument into the lateral cut guide to guide a lateral cut in the femur.

Example 15 is a method that can include: outputting, by a computing device, an image representing a portion of a femur including a femoral prosthesis; receiving, by the computing device, input indicating one or more anatomical landmarks of the femur represented in the image; determining, by the computing device, a length of a longitudinal cut for an extended trochanteric osteotomy (ETO) based on the input indicating the one or more anatomical landmarks; and outputting, by the computing device, a representation of the determined length of the longitudinal cut.

In Example 16, the method of Example 15, further comprising determining, by the computing device, a location of a cut line for the ETO, wherein the cut line corresponds to the longitudinal cut and a lateral cut for the ETO.

In Example 17, the method of Example 16, further comprising outputting, by the computing device, a representation of the cut line relative to the femur represented in the image.

In Example 18, the method of any of Examples 15-17, further comprising outputting, by the computing device, a representation of the one or more anatomical landmarks relative to the femur represented in the image.

In Example 19, the method of any of Examples 15-18, further comprising outputting, by the computing device, an image representing an adjustable ETO cut guide, the image comprising the one or more anatomical landmarks relative to the cut guide.

In Example 20, the method of any of Examples 15-19, further comprising outputting, by the computing device, an image representing an adjustable ETO cut guide, the image comprising the one or more anatomical landmarks relative to the cut guide.

In Example 21, the method of any of Examples 15-20, further comprising transforming, by the computing device, the determined length of the longitudinal cut to a length index value and outputting the length index value as the representation of the determined length of the longitudinal cut.

In Example 22, the method of Example 21, wherein the length index value corresponds to a length index of an adjustable ETO cut guide employed for the ETO.

In Example 23, the method of any of Examples 15-19, wherein the one or more anatomical landmarks respectively correspond to one or more of a greater trochanter, a lesser trochanter, and a tip of a stem of the femoral prosthesis.

Example 24 is a method that can include: outputting, by a computing device, an image representing a portion of a femur including a femoral prosthesis; receiving, by the computing device, input indicating a location of a tip of a stem of the femoral prosthesis in the image; determining, by the computing device, a fixation zone for a revision femoral prosthesis based on the input indicating the location of the tip of the stem and based on at least one of a nominal fixation zone width and a nominal fixation zone length; determining, by the computing device, a recommended size of the revision femoral prosthesis based on the determined fixation zone; and outputting, by the computing device, the recommended size of the revision femoral prosthesis.

In Example 25, the method of Example 24, wherein the determined fixation zone comprises an initial fixation zone and further comprising: receiving, by the computing device, input indicating a change in a size of the initial fixation zone; and determining, by the computing device, a final fixation zone based on the input indicating the change in the size of the initial fixation zone, wherein determining, by the computing device, the recommended size of the revision femoral prosthesis comprises determining the recommended size of the revision femoral prosthesis based on the determined final fixation zone.

Example 26 is a method that can include: outputting, by a computing device, an image representing a portion of a femur including a femoral prosthesis; receiving, by the computing device, input indicating one or more anatomical landmarks of the femur represented in the image, the one or more anatomical landmarks comprising a location of a tip of a stem of the femoral prosthesis in the femur; determining, by the computing device, a length of a longitudinal cut for an extended trochanteric osteotomy (ETO) based on the input indicating the one or more anatomical landmarks; outputting, by the computing device, a representation of the determined length of the longitudinal cut; determining, by the computing device, a fixation zone for a revision femoral prosthesis based on the input indicating the location of the tip of the stem and based on at least one of a nominal fixation zone width and a nominal fixation zone length; determining, by the computing device, a recommended size of the revision femoral prosthesis based on the determined fixation zone; and outputting, by the computing device, the recommended size of the revision femoral prosthesis.

Example 27 is a method that can include: outputting, by a computing device, an image representing a portion of a femur including a femoral prosthesis; receiving, by the computing device, input indicating one or more anatomical landmarks of the femur represented in the image; determining, by the computing device, a length of a longitudinal cut for an extended trochanteric osteotomy (ETO) based on the input indicating the one or more anatomical landmarks; outputting, by the computing device, a representation of the determined length of the longitudinal cut; attaching an adjustable cut guide device to the proximal end of the femur, the cut guide device comprising: a first member configured to be attached to the proximal end of the femur; and a second member movably attached to the first member, the second member comprising a longitudinal cut guide and a lateral cut guide; and moving the second member relative to the first member to set a length of the longitudinal cut guide to the determined length of the longitudinal cut.

Example 28 is a method that can include: outputting, by a computing device, an image representing a portion of a femur including a femoral prosthesis; receiving, by the computing device, input indicating one or more anatomical landmarks of the femur represented in the image, the one or more anatomical landmarks comprising a location of a tip of a stem of the femoral prosthesis in the femur; determining, by the computing device, a length of a longitudinal cut for an extended trochanteric osteotomy (ETO) based on the input indicating the one or more anatomical landmarks; outputting, by the computing device, a representation of the determined length of the longitudinal cut; determining, by the computing device, a fixation zone for a revision femoral prosthesis based on the input indicating the location of the tip of the stem and based on at least one of a nominal fixation zone width and a nominal fixation zone length; determining, by the computing device, a recommended size of the revision femoral prosthesis based on the determined fixation zone; outputting, by the computing device, the recommended size of the revision femoral prosthesis; attaching an adjustable cut guide device to the proximal end of the femur, the cut guide device comprising: a first member configured to be attached to the proximal end of the femur; and a second member movably attached to the first member, the second member comprising a longitudinal cut guide and a lateral cut guide; and moving the second member relative to the first member to set a length of the longitudinal cut guide to the determined length of the longitudinal cut.

Templating software and associated methods in accordance with this disclosure can be implemented in a variety of hardware, software, and hardware and software systems. Such systems can include a standalone computing device or devices or one or more client computing devices, servers, data repositories, and other devices communicatively connected over a network. The computing device(s) on which the software is implemented can include any number of different portable electronic mobile devices, including, e.g., cellular phones, personal digital assistants (PDA's), laptop computers, as well as non-portable devices such as desktop computers. The computing device(s) can include one or more input/output devices, e.g., mouse, stylus, display device, etc., configured to allow user interaction with one or more software programs executed by the computing device(s).

The templating software and associated computing devices can be implemented with a combination of hardware and software including one or more processors and storage devices. One or more processors can be configured to implement functionality of the software and/or process instructions for execution within a computing device. For example, one or more processors can be configured to process instructions stored at one or more storage devices, which include, in some examples, instructions for executing functions attributed to example templating software in accordance with this disclosure. Examples of processors include any one or more of a microprocessor, a controller, a digital signal processor (DSP), an application specific integrated circuit (ASIC), a field-programmable gate array (FPGA), or equivalent discrete or integrated logic circuitry. Example storage devices include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Various examples have been described. These and other examples are within the scope of the following claims.

The invention claimed is:

1. A method comprising:
outputting, by a computing device, an image representing a portion of a femur including a femoral prosthesis;
receiving, by a processor associated with the computing device, input indicating one or more anatomical landmarks of the femur represented in the image;
determining, by the processor, a length of a longitudinal cut to be performed during an extended trochanteric osteotomy (ETO), wherein the processor includes logic circuitry, and wherein the determining is based on the input indicating the one or more anatomical landmarks; and
outputting, by the computing device, a representation of the determined length of the longitudinal cut to be performed during an ETO.

2. The method of claim 1, further comprising determining, by the computing device, a location of a cut line for the ETO, wherein the cut line corresponds to the longitudinal cut and a lateral cut for the ETO.

3. The method of claim 2, further comprising outputting, by the computing device, a representation of the cut line relative to the femur represented in the image.

4. The method of claim 1, further comprising outputting, by the computing device, a representation of the one or more anatomical landmarks relative to the femur represented in the image.

5. The method of claim 1, further comprising outputting, by the computing device, an image representing an adjustable ETO cut guide, the image comprising the one or more anatomical landmarks relative to the cut guide.

6. The method of claim 1, further comprising outputting, by the computing device, an image representing an adjustable ETO cut guide, the image comprising the one or more anatomical landmarks relative to the cut guide.

7. The method of claim 1, further comprising transforming, by the computing device, the determined length of the longitudinal cut to a length index value and outputting the length index value as the representation of the determined length of the longitudinal cut.

8. The method of claim 7, wherein the length index value corresponds to a length index of an adjustable ETO cut guide employed for the ETO.

9. The method of claim 1, wherein the one or more anatomical landmarks respectively correspond to one or more of a greater trochanter, a lesser trochanter, and a tip of a stem of the femoral prosthesis.

10. A method comprising:
outputting, by a computing device, an image representing a portion of a femur including a femoral prosthesis;
receiving, by a processor associated with the computing device, input indicating a location of a tip of a stem of the femoral prosthesis in the image;
determining, by the processor, a fixation zone for a revision femoral prosthesis, wherein the processor includes a logic circuitry, and wherein the determining a fixation zone for a revision femoral prosthesis is based on the input indicating the location of the tip of the stem and based on at least one of a nominal fixation zone width and a nominal fixation zone length;
determining, by the processor, a recommended size of the revision femoral prosthesis based on the determined fixation zone; and
outputting, by the computing device, the recommended size of the revision femoral prosthesis to be performed during an ETO.

11. The method of claim 10, wherein the determined fixation zone comprises an initial fixation zone and further comprising:
receiving, by the computing device, input indicating a change in a size of the initial fixation zone; and
determining, by the computing device, a final fixation zone based on the input indicating the change in the size of the initial fixation zone,
wherein determining, by the computing device, the recommended size of the revision femoral prosthesis comprises determining the recommended size of the revision femoral prosthesis based on the determined final fixation zone.

* * * * *